US005753625A

United States Patent [19]

Buelow

[11] Patent Number: 5,753,625
[45] Date of Patent: May 19, 1998

[54] TREATMENT FOR INHIBITING THE PROGRESSION OF AUTOIMMUNE DISEASE

[75] Inventor: Roland Buelow, Palo Alto, Calif.

[73] Assignee: SangStat Medical Corporation, Menlo Park, Calif.

[21] Appl. No.: 440,504

[22] Filed: May 12, 1995

[51] Int. Cl.[6] .................. A61K 38/00; A61K 38/02; C07K 5/00; C07K 7/00
[52] U.S. Cl. .................. 514/13; 514/14; 514/15; 514/16; 514/17
[58] Field of Search .................. 514/13, 14, 15, 514/16, 17

[56] References Cited

FOREIGN PATENT DOCUMENTS

WO9010016  9/1990  WIPO .................. C07K 7/06
WO93/17699 9/1993  WIPO .

OTHER PUBLICATIONS

Nisco et al., *Journal of Immunology*, 1994, pp. 3786–3792, vol. 152.
Stagsted et al., *Cell*, vol. 62, pp. 297–307.
Cuturi et al., Prolongation of Allogeneic Heart Graft Survival in Rats by Administration of a Peptide (a.a. 75–84) From the α1 Helix of the First Domain of HLA–B7 01 (1995) *Transplantation*, vol. 59, No. 5:661–669.

Buelow et al., Immunomodulation by Soluble HLA Class I (1995) *Transplantation*, vol. 59, No. 5:649–654.

Buelow et al., Prolongation of Skin Allograft Survival in Mice Following Administration of Allotrap[1] (1995) *Tranplantation*, vol. 59, No. 4:455–460.

Stagsted et al., Regulation of Insulin Receptor Functions by a Peptide Derived from a Major Histocompatibility Complex Class I Antigen (1990) *Cell*, vol. 62:297–307.

Nisco et al., Induction of Allograft Tolerance in Rats by an HLA Class–I–Derived Peptide and Cyclosporine A[1] (1994) *J. of Immunology*.

Kabat et al., (1991) *Sequences of Proteins of Immunological Interest*, NIH publication No. 91–3242, vol. 1:738–740, 761, 770–771, 779–780, 788–789 and 802–804.

*Primary Examiner*—Avis M. Davenport
*Attorney, Agent, or Firm*—Flehr Hohbach Test Albritton & Herbert LLP

[57] ABSTRACT

The progression of autoimmune disease is inhibited by the administration of peptides having the sequence of MHC Class I antigen α1-domains. These fragments include the amino acids between positions 70 and 91 of the MHC Class I antigens. The onset of IDDM is significantly decreased by the subject treatment.

8 Claims, 2 Drawing Sheets

TREATMENT FOR INHIBITING THE PROGRESSION OF AUTOIMMUNE DISEASE

INTRODUCTION

1. Technical Field

The field of this invention is the regulation of autoimmune disease using peptide fragments.

2. Background

The complex immune system of mammals and birds must achieve a delicate balance, where pathogens are recognized and eliminated, but host cells are safe from immune destruction. Subtle environmental and genetic factors can disrupt this balance, sometimes resulting in autoimmune disease. Attack by autologous cells of the immune system can be directed to a number of different targets, and have been correlated with a large number of disorders. Among them are neural diseases, such as multiple sclerosis and myasthenia gravis, diseases of the joints, such as rheumatoid arthritis, attacks on nucleic acids, as observed with systemic lupus erythematosus and such other diseases as psoriasis, insulin dependent diabetes mellitus (IDDM), Sjogren's disease, and thyroid disease. These diseases have a variety of symptoms, varying from minor and irritating to life-threatening.

Despite the extensive research efforts that have been involved with elucidating the basis for these diseases, the diseases for the most part have been recalcitrant to an understanding of their etiology in the development of therapeutic modes. Many of the diseases are believed to be associated with lymphocytic involvement, which can result in attack and degradation of proteins, cytotoxicity, and the like.

Insulin dependent diabetes mellitus, IDDM, has been linked to specific alleles of Class II MHC antigens. In particular, associations have been found in the Caucasian population with the allele DQB1*0302 (DQ3.2). This evidence has suggested that there is a link between the activity of CD4+ T lymphocytes and the onset of IDDM. The delay in onset of disease achieved by administration of cyclosporin A, which specifically inhibits CD4+ T cells, has supported this view.

The NOD mouse spontaneously develops a disease closely resembling IDDM in histology and range of autoimmune responses, which disease is also linked to loci of MHC Class II antigens. Under appropriate circumstances, transfer of T cells can induce early disease in young NOD mice. In the course of disease, the loss of β cells in the pancreatic islets of Langerhans is preceded by a peri-islet infiltration of CD4+ T cells, followed by CD8+ cells and macrophages. Macrophages are also important mediators of the tissue damage.

The role of T-cell subsets in the pathogenesis of IDDM is a matter of controversy. Conflicting data have been published. In some experiments it has been shown that islet destruction can be mediated by CD4+ T cells alone. Others have reported that, in the absence of Class I MHC antigens, there was no development of disease.

There is a need to develop therapies which can aid a patient by diminishing the detrimental effects of an autoimmune disease or by substantially inhibiting its course of action. By intervening in the effects of T lymphocyte effector functions, there may be ways to protect the host from autoimmune diseases.

Relevant Literature

The sequences of known HLA and H-2 alleles may be found in Kabat et al. (1991) *Sequences of Proteins of Immunological Interest*, N.I.H. publication no. 91-3242, vol. I, pp. 738–740, 761, 770–771, 779–780, 788–789 and 802–804. The composition and uses of such peptides are further described in International application PCT/US93/01758. Stagsted et al. (1990) *Cell* 62: 297–307 disclose the regulation of insulin receptor functions by a peptide derived from an MHC Class I peptide. The peptides are further disclosed in International application PCT/US89/00876.

Nisco et al. (1994) *J. Immunol.* 152: 3786 demonstrate the induction of allograft tolerance in rats by an HLA Class I derived peptide and cyclosporin A. Similar tolerance in mice was shown by Beulow et al. (1995) *Transplantation* 59: 455–460. Prolongation of allogeneic heart graft survival in rats by administration of a peptide from the α1 helix of the first domain of HLA-B7 is described in Cuturi et al. (1995) *Transplantation* 59: 661–669. Immunomodulation by soluble Class I molecules is reviewed in Beulow et al. (1995) *Transplantation* 59: 649–654.

The role of CD8+ T cells in the pathogenesis of IDDM is discussed in Bradley et al. (1992) *Diabetes* 41: 1603–1608. Katz et al. (1993) *Eur. J. Immunol.* 23: 3358–3360 disclose the requirement for MHC Class I molecules in the development of insulitis in NOD mice. Miyazaki et al. (1992) *P.N.A.S.* 89: 9519–9523 demonstrate the prevention of insulitis by expression of MHC L molecules.

Treatment of diabetes with peptides of MHC Class II molecules is discussed in L. Adorini (1992) *J. Autoimmunity* 5: 73–81; Hurtenbach et al. (1993) *J. Exp. Med.* 177: 1499–1504; and Lock et al. (1991) *Sem. Immunol.* 3: 247–255.

The progression of disease for IDDM is reviewed in Foulis et al. (1986) *Diabetologia* 29: 267–274; Caillat-Zucman et al. (1992) *J. Clin. Invest.* 90: 2242–2250; Vandewalle (1993) *Diabetologia* 36: 1155–1162; and Karjalainen et al. (1989) *N. Engl. J. Med.* 320: 881–886. The association of human IDDM with various genetic markers is discussed in Davies et al. (1994) *Nature* 371: 130–136.

SUMMARY OF THE INVENTION

Methods and compositions for inhibiting the progression of autoimmune disease are provided, based on the administration of peptides having a sequence at least in part of an MHC Class I antigen α1-domain. These fragments include the sequence of amino acids between positions 70 to 91 of the MHC Class I antigens and are used to modulate T cell mediated attack on autologous target cells.

DESCRIPTION OF THE SPECIFIC EMBODIMENTS

Figure 1:
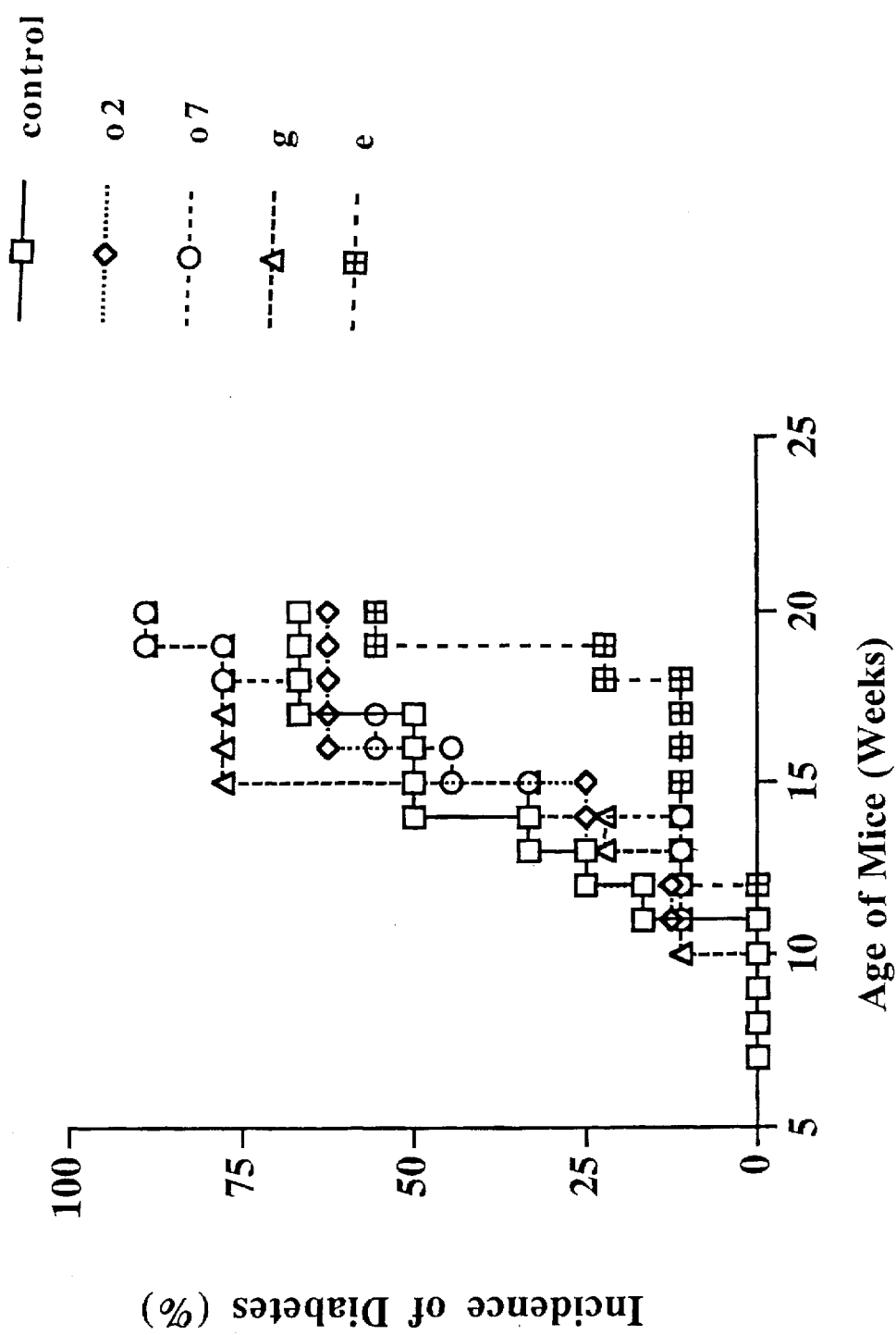
FIG. 1 is a graph depicting the effect of peptides administered by intravenous injection on the incidence of IDDM in female NOD mice.

The adverse effects of autoimmune disease are lessened by the administration of peptides having the sequence of MHC Class I antigen α1-domains. These fragments include the amino acids between positions 70 and 91 of the MHC Class I antigens. For a given locus, the amino acid sequence of this region has several invariant residues, and is otherwise generally conservative among different alleles. Between related species, i.e. among mammals, there are also sequence similarities in this region. Class I MHC antigens of interest include the human HLA-A, -B, -C, -E and -G, and murine H-2K and H-2D, and derivatives thereof.

A pharmaceutically acceptable formulation of the subject peptides is administered to a host suffering from an autoimmune disease. The data indicates that the treatment acts by reducing the severity of cytotoxic T lymphocyte mediated attack on autologous tissue. Generally the cytotoxic T lymphocytes will be CD8+. The effect is to spare the function of the autologous tissue which is the target of the autoreactive T lymphocytes. In addition, there may be a reduction in the inflammation, swelling, release of cytokines, perforins, granzymes, etc. which are associated with T cell activation.

One group of therapeutic compositions comprise oligopeptides of at least 6 amino acids comprising the tripeptide or triad (SEQ ID NO:1) TYR-TYR-TRP (YYW), preferably the tetrapeptide (SEQ ID NO:2) ARG-TRY-TYR-TRP (RYYW). At the N terminus of the tripeptide or tetrapeptide, there will usually be at least about 4 amino acids, more usually at least about 5 amino acids, where for the most part, the sequence of amino acids will be the sequence of the Class I HLA-B $\alpha_1$ domain, residues 80 to 86, more usually 78 to 86, frequently 75 to 86, or the equivalent thereof of other species, e.g. mouse, rat, etc. In some cases the sequence of amino acids will extend beyond residues 75 to 83, although as the oligopeptide is extended, an increasing number of substitutions from the natural sequences are permissible. The C terminus of the tripeptide or tetrapeptide may also be extended, usually by not more than 5 amino acids, more usually by not more than 3 amino acids, frequently not more than 1 amino acid.

For the most part, the oligopeptides will have at least 6, usually at least 8, amino acids and come within the following formula:

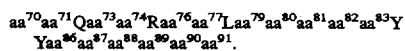

Wherein:

$aa^{70}$ is Q, H, S, N or K;

$aa^{71}$ is an aliphatic neutral amino acid, including S, A and T;

$aa^{73}$ is T or A;

$aa^{74}$ is D, Y or H;

$aa^{76}$ is V;

$aa^{77}$ is D, S or N;

$aa^{79}$ is R or G;

$aa^{80}$ is T, I, N or an aromatic amino acid, e.g., F, W or Y;

$aa^{81}$ is an aliphatic non-polar amino acid including L or A;

$aa^{82}$ is R, L or an aromatic amino acid, particularly L;

$aa^{83}$ is G or R;

$aa^{86}$ is W or N;

$aa^{87}$ is any amino acid, particularly neutral aliphatic or aromatic, G, A, S, T, M, N, Q, F, W, or Y, more particularly, A, W, F, N, Q, or S;

$aa^{88}$ is an aromatic amino acid or aliphatic amino acid of from 5 to 6 carbon atoms, particularly F, W, Y, L, I or V;

$aa^{89}$ is any amino acid, particularly neutral aliphatic or aromatic, G, A, S, T, M, N, Q, F, W, or Y, more particularly, A, W, F, N, Q, or S;

$aa^{90}$ is any amino acid, particularly neutral aliphatic or aromatic, G, A, S, T, M, N, Q, F, W, or Y, more particularly, A, W, F, N, Q, or S; and $aa^{91}$ is any amino acid, particularly neutral aliphatic or aromatic, G, A, S, T, M, N, Q, F, W, or Y, more particularly, A, W, F, N, Q, or S.

Desirably, for the amino acid sequence after position $aa^{86}$ (W), the sequence will alternate an aromatic amino acid with an aliphatic amino acid, particularly a neutral aliphatic amino acid.

Also of interest are compositions coming within the above formula, comprising the sequence from position 75 to 84.

For the most part, the peptides will be at least 6 amino acids, more usually at least 8 amino acids, frequently at least 10 amino acids and up to the entire sequence of 22 amino acids or the dimer of 44 amino acids for the active sequence. The active sequence may be bonded or non-covalently linked within a chain or as a side chain of other peptides or proteins, for a variety of purposes. The peptide may be cyclized by various methods, as known in the art.

Also included in the subject compositions are oligopeptide dimers, which may be head to head, tail to tail, or head to tail. In addition, 1 or more of the amino acids may be the D-stereoisomer, up to all of the amino acids.

Compositions of particular interest have the following formula: (SEQ ID NO:3) R N/D L R I A/L L R/E Y Y W Q/D S, where the backslashes intend that either amino acid may be present at that position. The preferred compositions will have at least 8 amino acids, preferably at least about 10 amino acids. The 10 amino acids may comprise a sequence within the above formula which includes the tripeptide YYW, desirably, terminating with W. Alternatively, the 10 amino acids may comprise the sequence (SEQ ID NO:16) R N/D L R I A/L L R/E Y.

For the most part, the peptides of the subject invention will employ the amino acids naturally found at the α1-domain, except as specifically indicated. While the combinations of amino acids may not be naturally found, the individual amino acid will usually be present in one or more α1 domains. One may have up to and including 2 mutations, usually not more than about 1 mutation, where the term "mutation" is intended to mean that one does not find that amino acid present at that particular position in the HLA-B α1-domain sequence, or the sequence of the analogous protein in other species, particularly mouse, excluding the tryptophan at amino acid 86 as coming within the number of mutations.

The subject peptides may be modified in a wide variety of ways. Sequence analogs may be prepared by oligopeptide synthesis using a stepwise substitution of the amino acids at each position with alanine or valine, particularly alanine. Generally the total number of amino acids substituted will not exceed 3, ranging from 1 to 3, usually 1 to 2. Methods of producing "scanning" mutatations are known in the art, and have been successfully used with a number of different peptides. Examples of protocols for scanning mutations may be found in Gustin, et al. (1993) *Biotechniques* 14: 22; Barany (1985) *Gene* 37: 111–23; Colicelli, et al. (1985) *Mol Gen Genet* 199: 537–9 and Prentki, et al. (1984) *Gene* 29: 303–13.

The peptides may be joined by covalent bonds at any convenient site along the peptide to a variety of other compounds for different purposes. Of particular interest is joining the subject peptides to another molecule by synthesis or expression of a synthetic gene where the other molecule provides for extended stability of the subject peptides when administered to a host. Various peptides may be used, such as the immunoglobulin constant region, e.g. IgG Fc, or the peptide may be joined to a lipid or polyalkyleneoxy group, to a sugar; or to a nucleic acid. The peptide may be PEGylated, where the polyethyleneoxy group provides for enhanced lifetime in the blood stream. One can prepare these compositions by preparing or isolating a gene coding for the particular peptide or protein, and joining that gene to a DNA sequence coding for the subject peptide. The gene may be introduced into an appropriate expression vector, there being many expression vectors commercially available, whereby the gene is then expressed in an appropriate host. See, Sambrook et al., Molecular Biology: A Laboratory Manual, Cold Spring Harbor Laboratories, Cold Spring Harbor, N.Y., 1989.

The peptides may be prepared in a variety of ways. Conveniently, they can be synthesized by conventional techniques employing automatic synthesizers, such as the Beckman, Applied Biosystem Inc., or other useful peptide synthesizer apparatus, or may be synthesized manually. Alternatively, DNA sequences can be prepared that encode the particular peptide and may be cloned and expressed to provide the desired peptide. In this instance a formyl-methionine may be the first amino acid, or repetitive sequences may be cleaved to produce the individual peptides. Unnatural amino acids may also be used, particular the D-isomer of naturally occurring amino acids, or a mixture of D- and L-isomers.

The peptides may also be isolated from natural sources and purified by known techniques, including, for example, chromatography on ion exchange materials, separation by size, immunoaffinity chromatography and electrophoresis. As used herein, the term "a substantially pure preparation of peptide compound" means a preparation of the peptide that is usually greater than about 75% free of materials with which the polypeptide is naturally associated, and usually greater than about 90% free of these materials; these materials, however, exclude materials with which the peptide may be mixed in the preparation of pharmaceutical compositions. Usually, the percentages will be based upon total protein. The sequences may be modified in a variety of ways depending upon their ultimate purpose. Different N- or C- terminal groups may be introduced which allow for linking of the peptide to solid substrates or other molecules, or for cyclization.

Chemical linking may be provided to various peptides or proteins comprising convenient functionalities for bonding, such as amino groups for amide or substituted amine formation, e.g. reductive amination, thiol groups for thioether or disulfide formation, carboxyl groups for amide formation, and the like. Of particular interest are peptides of at least 2, more usually 3 and not more than about 60 lysine groups, particularly polylysines of from about 4 to 20, usually 6 to 18 lysine units, referred to as MAP, where the subject peptides are bonded to the lysine amino groups, generally at least about 20%, more usually at least about 50%, of available amino groups, to provide a multipeptide product. Thus, when one obtains molecules having a plurality of the subject peptides where the orientation of the subject peptides is in the same direction, in effect one has a linking group to provide for tail to tail di- or oligomerization. Alternatively, other naturally occurring or synthetic peptides and proteins may be used to provide a backbone for attachment of the subject peptides at the C terminus.

The peptides will be administered to a host which is susceptible to an autoimmune disease. Of particular interest are primates, more particularly humans, but other mammals are also of interest, particularly domestic animals such as equine, bovine, ovine, feline, canine, murine, lagomorpha, and the like. The diseases of interest will be associated with T-cell mediated tissue destruction. Included are multiple sclerosis, rheumatoid arthritis, psoriasis, pemphigus vulgaris, Sjogren's disease, thyroid disease, Hashimoto's thyroiditis, myasthenia gravis, as well as many others. Of particular interest is insulin dependent diabetes mellitus (IDDM), also known as juvenile onset or Type I diabetes, associated with destruction of beta cells in the pancreatic islets of Langerhans.

The peptide composition will desirably be administered during the presymptomatic or preclinical stage of the disease, and in some cases during the symptomatic stage of the disease. Early treatment is preferable, in order to prevent the loss of function associated with autoimmune tissue damage. The presymptomatic, or preclinical stage will be defined as that period not later than when there is T cell involvement at the site of disease, e.g. islets of Langerhans, synovial tissue, thyroid gland, etc., but the loss of function is not yet severe enough to produce the clinical symptoms indicative of overt disease. T cell involvement may be evidenced by the presence of elevated numbers of T cells at the site of disease, the presence of T cells specific for autoantigens, the release of perforins and granzymes at the site of disease, response to immunosuppressive therapy, etc.

Using IDDM as an example, overt diabetes occurs when the level of glucose in the blood rises above a specific level, usually about 250 mg/dl. In humans a long presymptomatic period precedes the onset of diabetes. During this period there is a gradual loss of pancreatic β cell function. The disease progression may be monitored in individuals diagnosed by family history and genetic analysis as being susceptible. The most important genetic effect is seen with genes of the major histocompatibility locus (IDDM1), although other loci, including the insulin gene region (IDDM2) also show linkage to the disease (see Davies et al, supra and Kennedy et al. (1995) *Nature Genetics* 9: 293–298). Markers that may be evaluated during the presymptomatic stage are the presence of insulitis in the pancreas, the level and frequency of islet cell antibodies, islet cell surface antibodies, aberrant expression of Class II MHC molecules on pancreatic β cells, glucose concentration in the blood, and the plasma concentration of insulin. An increase in the number of T lymphocytes in the pancreas, islet cell antibodies and blood glucose is indicative of the disease, as is a decrease in insulin concentration. After the onset of overt diabetes, patients with residual β cell function, evidenced by the plasma persistence of insulin C-peptide, may also benefit from administration of the subject peptides in order to prevent further loss of function.

In multiple sclerosis, the overt disease is associated with muscle weakness, loss of abdominal reflexes, visual defects and paresthesias. During the presymptomatic period there is infiltration of leukocytes into the cerebrospinal fluid, inflammation and demyelination. Family histories and the presence of the HLA haplotype DRB1*1501, DQA1*0102, DQB1*0602 are indicative of a susceptibility to the disease. Markers that may be monitored for disease progression are the presence of antibodies in the cerebrospinal fluid, "evoked potentials" seen by electroencephalography in the visual cortex and brainstem, and the presence of spinal cord defects by MRI or computerized tomography. Treatment during the early stages of the disease will slow down or arrest the further loss of neural function.

Rheumatoid arthritis is evidenced in the overt disease by severe inflammation and pain in the affected joints, produced by the malign growth of synovial cells. Virtually all patients have circulating titer of autoantibodies to the Fc region of IgG. Treatment with the subject peptides during early stages is desirable.

The host may be treated with one or several peptides chosen from the previously defined group. The choice of peptides from within the group may be empirically derived. An assay of particular interest for determining the choice of peptide will draw peripheral blood from the host, and determine whether a specific peptide inhibits the ability of the CD8+ T lymphocytes to differentiate and lyse target cells. Such assays have been previously described (see Clayberger et al. [1993] *Transplant. Proc.* 25: 477). The peptide(s) which demonstrate in vitro activity with a particular host will then be administered. It has been found that with particular genetic backgrounds, certain peptide sequences will not be active, as shown in the examples. Such peptides may have show in vivo activity in conjunction with other genetic backgrounds.

Peptides that are active with a number of different alleles are of particular interest. The screening assay may be performed with a number of different peripheral blood samples in order to determine whether the activity is maintained with cells of different haplotypes. The peptide(s) that demonstrate activity with a number of different hosts will be selected for use.

Desirably, the peptides should not induce an immune response, particularly an antibody response. Xenogeneic or mutated analogs of the native sequence may be screened for their ability provide a therapeutic effect without raising an immune response.

Various methods for administration may be employed. The peptide formulation may be given orally, or may be injected intravascularly, subcutaneously, peritoneally, etc. The dosage of the therapeutic formulation will vary widely, depending upon the nature of the disease, the frequency of administration, the manner of administration, the clearance of the agent from the host, and the like. The initial dose may be larger, followed by smaller maintenance doses. For example, a dose of 1 to 100 mg peptide/kg body weight/ week has been shown to be effective in delaying the onset of IDDM. For the treatment of IDDM, blood glucose will be monitored regularly to determine the efficacy of the treatment. The dose may be administered as infrequently as weekly or biweekly, or fractionated into smaller doses and administered daily, semi-weekly, etc. to maintain an effective dosage level of peptide. In many cases, oral administration will require a higher dose than if administered intravenously. The amide bonds, as well as the amino and carboxy termini, may be modified for greater stability on oral administration.

The subject peptides may be prepared as formulations at a pharmacologically effective dose in pharmaceutically acceptable media, for example normal saline, PBS, etc. The additives may include bactericidal agents, stabilizers, buffers, or the like. In order to enhance the half-life of the subject peptide or subject peptide conjugates, the peptides may be encapsulated, introduced into the lumen of liposomes, prepared as a colloid, or another conventional technique may be employed that provides for an extended lifetime of the peptides.

The peptides may be administered as a combination therapy with other pharmacologically active agents. The additional drugs may be administered separately or in conjunction with the peptide compositions, and may be formulated in the same formulation. Of particular interest are immunosuppressive agents, particularly those that are targeted to CD4+ T lymphocytes, e.g. cyclosporins, FK-506, rapamycin, etc.

The following examples are offered by way of illustration and not by limitation.

EXAMPLES

Delay of Onset of IDDM in NOD Mice following Administration of Peptides

Peptides: The following peptides, which have an amino acid sequence corresponding to a portion of the α-1 domain of MHC class I antigens, were synthesized by an automated peptide synthesizer using Fmoc chemistry. Peptides were purified by preparative reverse phase HPLC and shown to be greater than 95% homogeneous by analytical reverse phase HPLC. Amino acid content was confirmed by amino acid analysis. The peptide sequences are shown in Table 1. The class I MHC antigens of the NOD mouse, $H-2K^d$ and $H-2D^b$ are shown.

TABLE 1

| | Corresponding allele | Amino acid residues | | | | | | | | | | Reference |
|---|---|---|---|---|---|---|---|---|---|---|---|---|
| | | 75 | 76 | 77 | 78 | 79 | 80 | 81 | 82 | 83 | 84 | |
| PEPTIDE 2702 (SEQ ID NO: 4) | HLA-B2702 | R | E | N | L | R | I | A | L | R | Y | 1 |
| PEPTIDE 07 (SEQ ID NO: 7) | HLA-B7 | R | E | S | L | R | N | L | R | G | Y | 1 |
| PEPTIDE E (SEQ ID NO: 8) | HLA-E | R | V | N | L | R | T | L | R | R | Y | 2 |
| PEPTIDE G (SEQ ID NO: 11) | HLA-G | R | M | N | L | Q | T | L | R | G | Y | 3 |
| PEPTIDE $K^{ka}$ (SEQ ID NO: 12) | $H-2\ K^{k(a)}$ | R | V | N | L | R | T | A | L | R | Y | 4 |
| PEPTIDE $K^{kb}$ (SEQ ID NO: 13) | $H-2\ K^{k(b)}$ | R | V | S | L | R | T | A | L | R | Y | 5 |
| PEPTIDE $D^k$ (SEQ ID NO: 14) | $H-2\ D^k$ | R | V | D | L | R | T | L | L | R | Y | 5 |
| PEPTIDE $K^b$ (SEQ ID NO: 9) | $H-2\ K^b$ | R | V | D | L | R | T | L | L | G | Y | 6 |
| PEPTIDE $D^b$ (SEQ ID NO: 10) | $H-2\ D^b$ | R | V | S | L | R | N | L | L | G | Y | 5 |
| PEPTIDE $K^d$ (SEQ ID NO: 15) | $H-2\ K^d$ | R | V | S | L | R | T | A | Q | R | Y | 7 |

References:
1 Zemmour and Parham (1992) Immunogenetics 37:239.
2 Koller et al. (1988) J. Immunol. 141:897.
3 Heinrichs et al. (1990) Immunol. Res. 9:265.
4 Minamide et al. (1988) Immunogenetics 27:148.
5 Watts et al (1987) J. Immunol. 139:3878.
6 Reyes et al. (1982) P.N.A.S. 79:3270.
7 Kabat, supra.

Treatment: In experiment I, 1 mg of PEPTIDE 07 (SEQ ID NO:7), 2702 (SEQ ID NO:4), E (SEQ ID NO:8) or G (SEQ ID NO:11) formulated in normal saline was administered intravenously once a week for a period of 8 weeks. All animals were 8 weeks old at the beginning of the experiment. In experiment II, 0.3 mg of PEPTIDE E (SEQ ID NO:8), $D^b$ (SEQ ID NO:10) or $K^b$ (SEQ ID NO:9) were administered intraperitoneally three times a week until the onset of diabetes. All animals were five weeks old at the beginning of the experiment.

Determination of Blood Glucose: the blood glucose level in the blood of animals was determined once a week. 50 μl of blood from the tip of the tail was used for the blood glucose determination using a Johnson and Johnson glucose meter, according to the manufacturer's instructions. Animals with blood glucose levels greater than 250 mg/dl were considered to be diabetic.

Results: In experiment I, peptides were administered to 5 week old female NOD mice. The treatment was repeated weekly for a total of 8 weeks. 70% of control untreated female NOD mice developed diabetes by the age of 16 weeks. There was no statistically significant difference from the controls in animals that were treated with PEPTIDE 07 (SEQ ID NO:7), 2702 (SEQ ID NO:4) or G (SEQ ID NO: 11). Animals that were treated with PEPTIDE E (SEQ ID NO:8) showed a significant delay in the onset of IDDM (p<0.03). Only 10% of the animals treated with PEPTIDE E (SEQ ID NO:8) developed diabetes during the treatment period. After termination of treatment, 60% of the animals became diabetic by week 19. The data for experiment I is shown in FIG. 1.

Figure 2:
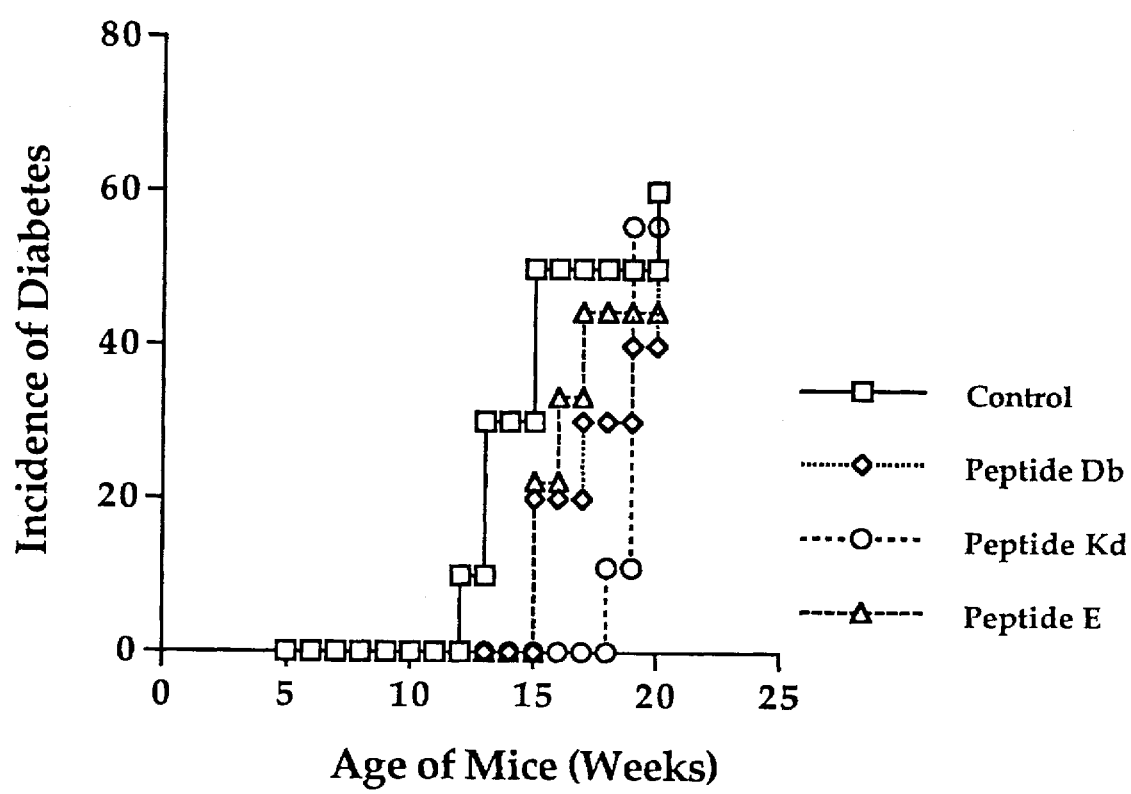
FIG. 2 is a graph depicting the effect of peptides administered by intraperitoneal injection.

In experiment II, 0.3 mg of PEPTIDE E (SEQ ID NO:8), $D^b$ (SEQ ID NO:10) or $K^b$ (SEQ ID NO:9) was administered three times per week intraperitoneally. The mice were 5 weeks old at the beginning of the treatment period, and treatment was continued until the development of diabetes. Using this protocol, the delay of onset of diabetes with PEPTIDE E (SEQ ID NO:8) appeared to be less pronounced, but was still statistically significant. Even with this treatment, PEPTIDE $K^b$ (SEQ ID NO:9) significantly delayed the onset of diabetes. The data for experiment II is shown in FIG. 2.

It is evident from the above results that peptides derived from a conserved region of the Class I MHC antigens can delay or prevent the onset of autoimmune disease. The subject methods provide a useful prophylaxis during the early stages of disease.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for affecting the course of an autoimmune disease involving T-cell mediated destruction of tissue, said method comprising:

administering to a mammalian host susceptible to said autoimmune disease, a peptide in an amount sufficient to modulate the activity of said T-cells; said peptide being an active sequence from about 6 to 22 amino acids in length and comprising the sequence:

$$aa^{70}aa^{71}Qaa^{73}aa^{74}R\ Vaa^{77}Laa^{79}aa^{80}aa^{81}aa^{82}aa^{83}Y\ Yaa^{86}aa^{87}aa^{88}aa^{89}aa^{90}aa^{91}.$$

Wherein:

$aa^{70}$ is Q, H, S, N or K;

$aa^{71}$ is an aliphatic neutral amino acid, including S, A and T;

$aa^{73}$ is T or A;

$aa^{74}$ is D, Y or H;

$aa^{77}$ is D, S or N;

$aa^{79}$ is R or G;

$aa^{80}$ is T, I, N or an aromatic amino acid, e.g., F, W or Y;

$aa^{81}$ is an aliphatic non-polar amino acid including L or A;

$aa^{82}$ is R, L or an aromatic amino acid, particularly L;

$aa^{83}$ is G or R;

$aa^{86}$ is W or N;

$aa^{87}$ is any amino acid, particularly neutral aliphatic or aromatic, G, A, S, T, M, N, Q, F, W, or Y, more particularly, A, W, F, N, Q, or S;

$aa^{88}$ is an aromatic amino acid or aliphatic amino acid of from 5 to 6 carbon atoms, particularly F, W, Y, L, I or V;

$aa^{89}$ is any amino acid, particularly neutral aliphatic or aromatic, G, A, S, T, M, N, Q, F, W, or Y, more particularly, A, W, F, N, Q, or S;

$aa^{90}$ is any amino acid, particularly neutral aliphatic or aromatic, G, A, S, T, M, N, Q, F, W, or Y, more particularly, A, W, F, N, Q, or S; and $aa^{91}$ is any amino acid, particularly neutral aliphatic or aromatic, G, A, S, T, M, N, Q, F, W, or Y, more particularly, A, W, F, N, Q, or S;

wherein the course of said autoimmune disease is affected.

2. A method according to claim 1, wherein said peptide is at least about 10 amino acids, and comprises the amino acid sequence shown as (SEQ ID NO:3).

3. A method according to claim 2, wherein said peptide is dimerized.

4. A method according to claim 2, wherein said peptide comprises at least one D-isomer amino acid.

5. A method according to claim 2, wherein said autoimmune disease is insulin dependent diabetes mellitus.

6. A method according to claim 5, wherein said administering is during the preclinical stage of said insulin dependent diabetes mellitus.

7. A method according to claim 6, wherein said peptide is selected from the group consisting of: (SEQ ID NO:12) RVNLRTLRRY; (SEQ ID NO:9) RVDLRTLLGY; and (SEQ ID NO:10) RVSLRNLLGY.

8. A method for inhibiting the course of insulin dependent diabetes mellitus (IDDM), said method comprising:

administering to a mammalian host susceptible to said IDDM, a peptide selected from the group consisting of: (SEQ ID NO:12) RVNLRTLRRY; (SEQ ID NO:9) RVDLRTLLGY; and (SEQ ID NO:10) RVSLRNLLGY;

wherein the course of said IDDM is inhibited.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 3 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

Tyr Tyr Trp
1

( 2 ) INFORMATION FOR SEQ ID NO:2:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:2:

Arg Tyr Tyr Trp
1

( 2 ) INFORMATION FOR SEQ ID NO:3:

(i) SEQUENCE CHARACTERISTICS:
: (A) LENGTH: 14 amino acids
: (B) TYPE: amino acid
: (C) STRANDEDNESS: single
: (D) TOPOLOGY: linear (ii) MOLECULE TYPE: protein (ix) FEATURE:
: (A) NAME/KEY: Modified-site
: (B) LOCATION: 2
: (D) OTHER INFORMATION: /note= "The 'X' at position can either be Valine or Glutamic Acid."

(ix) FEATURE:
: (A) NAME/KEY: Modified-site
: (B) LOCATION: 3
: (D) OTHER INFORMATION: /note= "The 'X' at position three can either be Asparagine or Aspartic Acid."

(ix) FEATURE:
: (A) NAME/KEY: Modified-site
: (B) LOCATION: 7
: (D) OTHER INFORMATION: /note= "The 'X' at position 7 can either be Alanine or Leucine."

(ix) FEATURE:
: (A) NAME/KEY: Modified-site
: (B) LOCATION: 9
: (D) OTHER INFORMATION: /note= "The 'X' at position 9 can either be Arginine or Glutamic Acid."

(ix) FEATURE:
: (A) NAME/KEY: Modified-site
: (B) LOCATION: 13
: (D) OTHER INFORMATION: /note= "The 'X' at position 13 can either be Glutamine or Aspartic Acid."

(xi) SEQUENCE DESCRIPTION: SEQ ID NO:3:

```
Arg Xaa Xaa Leu Arg Ile Xaa Leu Xaa Tyr Tyr Trp Xaa Ser
1               5                   10
```

(2) INFORMATION FOR SEQ ID NO:4:

(i) SEQUENCE CHARACTERISTICS:
: (A) LENGTH: 10 amino acids
: (B) TYPE: amino acid
: (C) STRANDEDNESS: single
: (D) TOPOLOGY: linear (ii) MOLECULE TYPE: protein (xi) SEQUENCE DESCRIPTION: SEQ ID NO:4:

```
Arg Glu Asn Leu Arg Ile Ala Leu Arg Tyr
1               5                   10
```

(2) INFORMATION FOR SEQ ID NO:5:

(i) SEQUENCE CHARACTERISTICS:
: (A) LENGTH: 10 amino acids
: (B) TYPE: amino acid
: (C) STRANDEDNESS: single
: (D) TOPOLOGY: linear (ii) MOLECULE TYPE: protein (xi) SEQUENCE DESCRIPTION: SEQ ID NO:5:

```
Arg Glu Asp Leu Arg Ile Ala Leu Arg Tyr
1               5                   10
```

(2) INFORMATION FOR SEQ ID NO:6:

(i) SEQUENCE CHARACTERISTICS:
: (A) LENGTH: 10 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:6:

```
Arg Glu Asn Leu Arg Ile Leu Leu Glu Tyr
1               5                   10
```

(2) INFORMATION FOR SEQ ID NO:7:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:7:

```
Arg Glu Ser Leu Arg Asn Leu Arg Gly Tyr
1               5                   10
```

(2) INFORMATION FOR SEQ ID NO:8:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:8:

```
Arg Val Asn Leu Arg Thr Leu Arg Arg Tyr
1               5                   10
```

(2) INFORMATION FOR SEQ ID NO:9:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:9:

```
Arg Val Asp Leu Arg Thr Leu Leu Gly Tyr
1               5                   10
```

(2) INFORMATION FOR SEQ ID NO:10:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:10:

```
Arg Val Ser Leu Arg Asn Leu Leu Gly Tyr
1               5                   10
```

(2) INFORMATION FOR SEQ ID NO:11:

(i) SEQUENCE CHARACTERISTICS:
(A) LENGTH: 10 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:11:

```
Arg Met Asn Leu Gln Thr Leu Arg Gly Tyr
1               5                   10
```

(2) INFORMATION FOR SEQ ID NO:12:

(i) SEQUENCE CHARACTERISTICS:
  (A) LENGTH: 10 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:12:

```
Arg Val Asn Leu Arg Thr Ala Leu Arg Tyr
1               5                   10
```

(2) INFORMATION FOR SEQ ID NO:13:

(i) SEQUENCE CHARACTERISTICS:
  (A) LENGTH: 10 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:13:

```
Arg Val Ser Leu Arg Thr Ala Leu Arg Tyr
1               5                   10
```

(2) INFORMATION FOR SEQ ID NO:14:

(i) SEQUENCE CHARACTERISTICS:
  (A) LENGTH: 10 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:14:

```
Arg Val Asp Leu Arg Thr Leu Leu Arg Tyr
1               5                   10
```

(2) INFORMATION FOR SEQ ID NO:15:

(i) SEQUENCE CHARACTERISTICS:
  (A) LENGTH: 10 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:15:

```
Arg Val Ser Leu Arg Thr Ala Gln Arg Tyr
1               5                   10
```

(2) INFORMATION FOR SEQ ID NO:16:

(i) SEQUENCE CHARACTERISTICS:
  (A) LENGTH: 10 amino acids

-continued

```
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Modified-site
        ( B ) LOCATION: 2
        ( D ) OTHER INFORMATION: /note= "The 'X' at position 2 can
                either be Valine or Glutamic Acid."

( i x ) FEATURE:
        ( A ) NAME/KEY: Modified-site
        ( B ) LOCATION: 3
        ( D ) OTHER INFORMATION: /note= "The 'X' at position 3 can
                either be Asparagine or Aspartic Acid."

( i x ) FEATURE:
        ( A ) NAME/KEY: Modified-site
        ( B ) LOCATION: 7
        ( D ) OTHER INFORMATION: /note= "The 'X' at position 7 can
                either be Alanine or Leucine."

( i x ) FEATURE:
        ( A ) NAME/KEY: Modified-site
        ( B ) LOCATION: 9
        ( D ) OTHER INFORMATION: /note= "The 'X' at position 9 can
                either be Arginine or Glutamic Acid."

( x i ) SEQUENCE DESCRIPTION: SEQ ID NO:16:

Arg  Xaa  Xaa  Leu  Arg  Ile  Xaa  Leu  Xaa  Tyr
 1                    5                      1 0
```